(12) United States Patent
Yu et al.

(10) Patent No.: US 8,025,050 B2
(45) Date of Patent: Sep. 27, 2011

(54) NEBULIZER AND CARTRIDGE STRUCTURE THEREOF

(75) Inventors: Shan-Yi Yu, Jhonghe (TW); Han-Chang Liu, Jhonghe (TW)

(73) Assignee: Health & Life Co., Ltd., Taipei (TW)

( * ) Notice: Subject to any disclaimer, the term of this patent is extended or adjusted under 35 U.S.C. 154(b) by 1313 days.

(21) Appl. No.: 11/595,905

(22) Filed: Nov. 13, 2006

(65) Prior Publication Data
US 2008/0122903 A1    May 29, 2008

(30) Foreign Application Priority Data

Nov. 8, 2006    (TW) .............................. 95219713 U (51) Int. Cl.
| | |
|---|---|
| A61M 15/00 | (2006.01) |
| A61M 11/00 | (2006.01) |
| A61M 15/08 | (2006.01) |
| A61M 16/00 | (2006.01) |
| B65D 88/54 | (2006.01) |
| B65D 5/72 | (2006.01) |
| B65D 35/22 | (2006.01) |
| B65D 43/04 | (2006.01) |
| B41J 2/17 | (2006.01) |
| B41J 2/175 | (2006.01) |

(52) U.S. Cl. ......... 128/200.14; 128/203.12; 128/203.15; 128/200.16; 128/200.23; 128/203.22; 128/203.23; 128/203.24; 128/203.25; 128/203.26; 222/325; 222/326; 222/327; 222/490; 222/94; 347/84; 347/86; 220/800; 220/801

(58) Field of Classification Search ............. 128/203.12, 128/203.15, 200.14, 200.16, 200.23, 203.22, 128/203.23, 203.24, 203.25, 203.26; 222/325, 222/326, 327, 490, 94, 129, 130, 132, 135, 222/383.3, 387, 492, 493, 499, 522; 347/86, 347/84; 220/800, 801
See application file for complete search history.

(56) References Cited

U.S. PATENT DOCUMENTS

7,591,400 B2 *   9/2009   Penciu et al. ................. 222/325
* cited by examiner

*Primary Examiner* — Justine Yu
*Assistant Examiner* — Nihir Patel
(74) *Attorney, Agent, or Firm* — Muncy, Geissler, Olds & Lowe, PLLC (57) ABSTRACT

A nebulizer and cartridge structure thereof for use in a nebulization apparatus comprises a first cartridge accommodation space and a second cartridge accommodation space. The first cartridge accommodation space includes at least one connection bottom, and the second cartridge accommodation space includes at least one connection side. Moreover, the second cartridge accommodation space is disposed under a lower connection position of the first cartridge accommodation space. The connection bottom is connected to the connection side to form an included angle that can be a lead angle. The lead angle further includes a fillet angle or a chamfering angle. Accordingly, the nebulizer and the cartridge structure can efficiently reduce the residues of liquid medicament.

6 Claims, 10 Drawing Sheets

Background Art

NEBULIZER AND CARTRIDGE STRUCTURE THEREOF

FIELD OF THE INVENTION

The present invention generally relates to a nebulizer and cartridge structure thereof, and more specifically relates to the nebulizer with a specific cartridge structure.

BACKGROUND OF THE INVENTION

Figure 1:
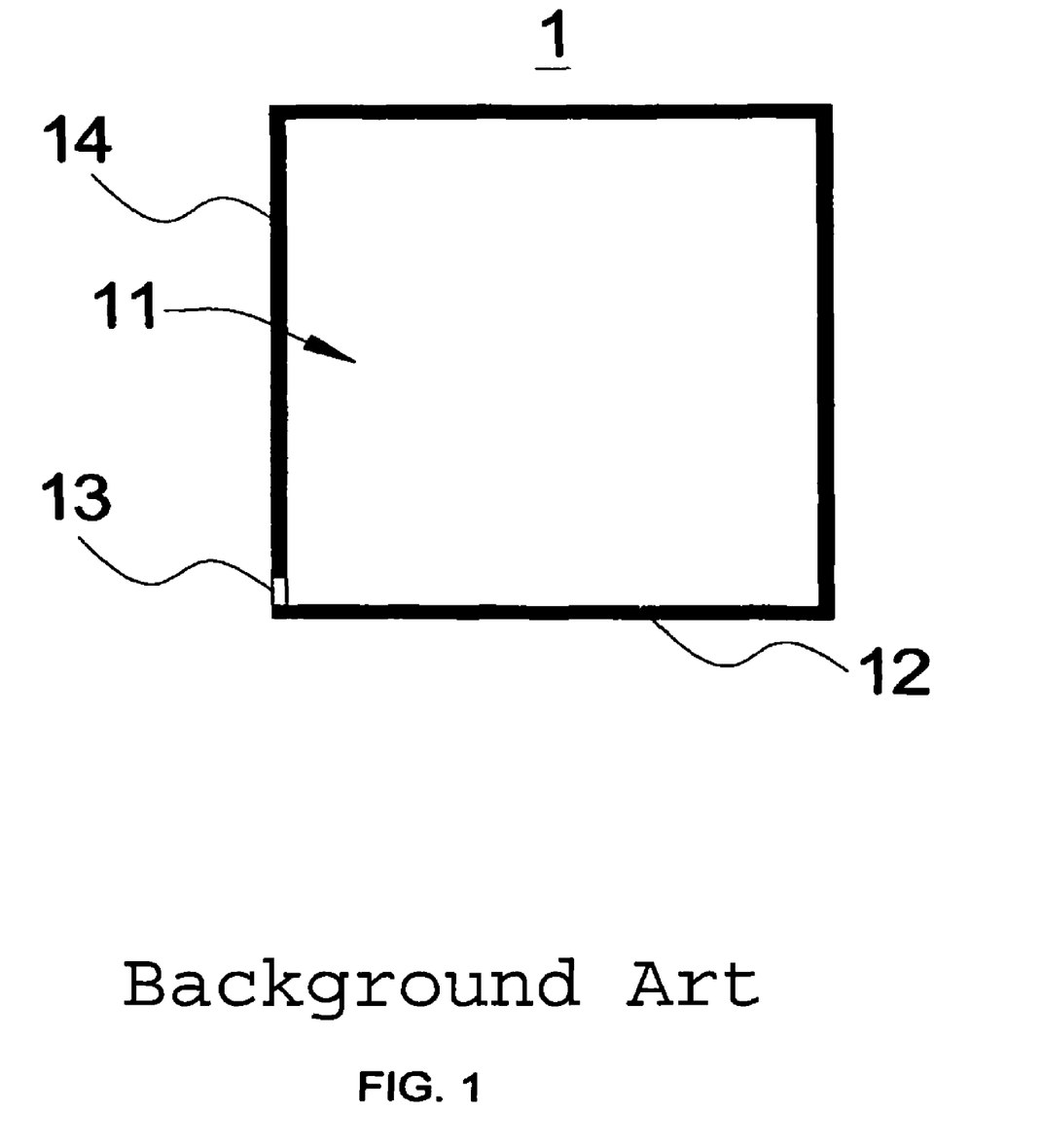
FIG. 1 is a schematic view of a cartridge structure of a prior art nebulizer.

The atomization method is often used to treat respiratory diseases. The method can be achieved by using a nebulizer, and particles sprayed by the nebulizer are droplets that are about 3~5 μm. For example, liquid medicaments can reach bronchus and lungs for therapy. The procedure is that aerosolized particles from liquid medicament are inhaled by the mouth and nose to enter bronchus, and the particles then are spread to the whole alveolus so that liquid medicament can be sufficiently absorbed by the human body. This way is better than oral administration. Currently, the atomization way adapted by nebulizers usually includes pneumatic atomization, ultrasonic atomization or electronic aerosol technology (e.g., piezoelectric nozzle method) for the operating mechanism of the nebulizer. As shown in FIG. 1, a cartridge structure 1 for accommodating liquid medicament for use in a conventional nebulizer comprises an accommodation space 11, a bottom 12, a side 14 and an opening 13. The bottom 12 is disposed to the bottom of the accommodation space 11, and the side 14 is vertically connected to the bottom, and the opening 13 is disposed to the position of the side 14 near the bottom 12. The opening 13 is an outlet for liquid medicament. When the opening 13 is at the position near the bottom 12, liquid medicament can be supplied by the accommodation space 11 to the opening 13.

Although residues of liquid medicament can be reduced through the opening 13 at the position near the bottom, it may be restricted by the entire structure of the accommodation space 11. Therefore, a portion of liquid medicament may be remained to the bottom of the accommodation space 11 to waste liquid medicament.

To overcome the foregoing shortcomings, the inventors of the present invention based on years of experience in the related field to conduct extensive researches and experiments, and finally invented a nebulizer and cartridge structure thereof as a method or a basis for overcoming the aforementioned problems.

SUMMARY OF THE INVENTION

A primary object of the present invention is to provide a nebulizer and cartridge structure thereof applying to medical equipment to efficiently eliminate the residues of liquid medicament through the specific cartridge structure.

To achieve of the foregoing object, the nebulizer comprises the cartridge structure and a nebulization apparatus, wherein the cartridge structure includes a first cartridge accommodation space and a second cartridge accommodation space. The first cartridge accommodation space includes at least one connection bottom and a lower connection position. The second cartridge accommodation space includes at least one connection side and an opening. The lower connection position of the first cartridge accommodation space is connected to the second cartridge accommodation space. Moreover, the connection bottom of the first cartridge accommodation space is connected to the connection side of the second cartridge accommodation space to form an included angle that is preferably a lead angle. The lead angle includes a chamfering angle or a fillet angle. Furthermore, nebulization apparatus includes a nebulizer main body, a nozzle disc and a vibratable member. The nebulizer main body has a controlling element, the nozzle disc is disposed to the opening of the second cartridge accommodation space, and the vibratable member is combined with the nozzle disc and electrically connected to the controlling element.

Accordingly, the volume of the first cartridge accommodation space is greater than the volume of the second cartridge accommodation space. The nebulization apparatus further uses a housing to cover up the nozzle disc and the vibratable member. The structure formed by the connection side of the second cartridge accommodation space and the connection bottom of the first cartridge accommodation space can be the combination of geometry. For instance, the connection bottom downwardly inclines toward the connection side to form an inclination, and the connection side can downwardly incline toward the lower portion of the second cartridge accommodation space to form a cambered surface. Alternatively, the bottom of the second cartridge accommodation space downwardly inclines toward the opening.

The nebulizer and its cartridge structure disclosed by the present invention can efficiently reduce the residues of liquid medicament to avoid the waste of liquid medicament.

To make it easier for our examiner to understand the object of the invention, its innovative features and performance, a detailed description and technical characteristics of the present invention are described together with the drawings as follows.

DETAILED DESCRIPTION OF THE PREFERRED EMBODIMENTS

Referring to the related figures for the nebulizer and the cartridge structure according to a preferred embodiment of the present invention, wherein the same elements are described by the same reference numerals.

Referring to FIG. 2 to FIG. 8 for the schematic diagrams of a cartridge structure according to a preferred embodiment of the invention is illustrated.

Figure 2:
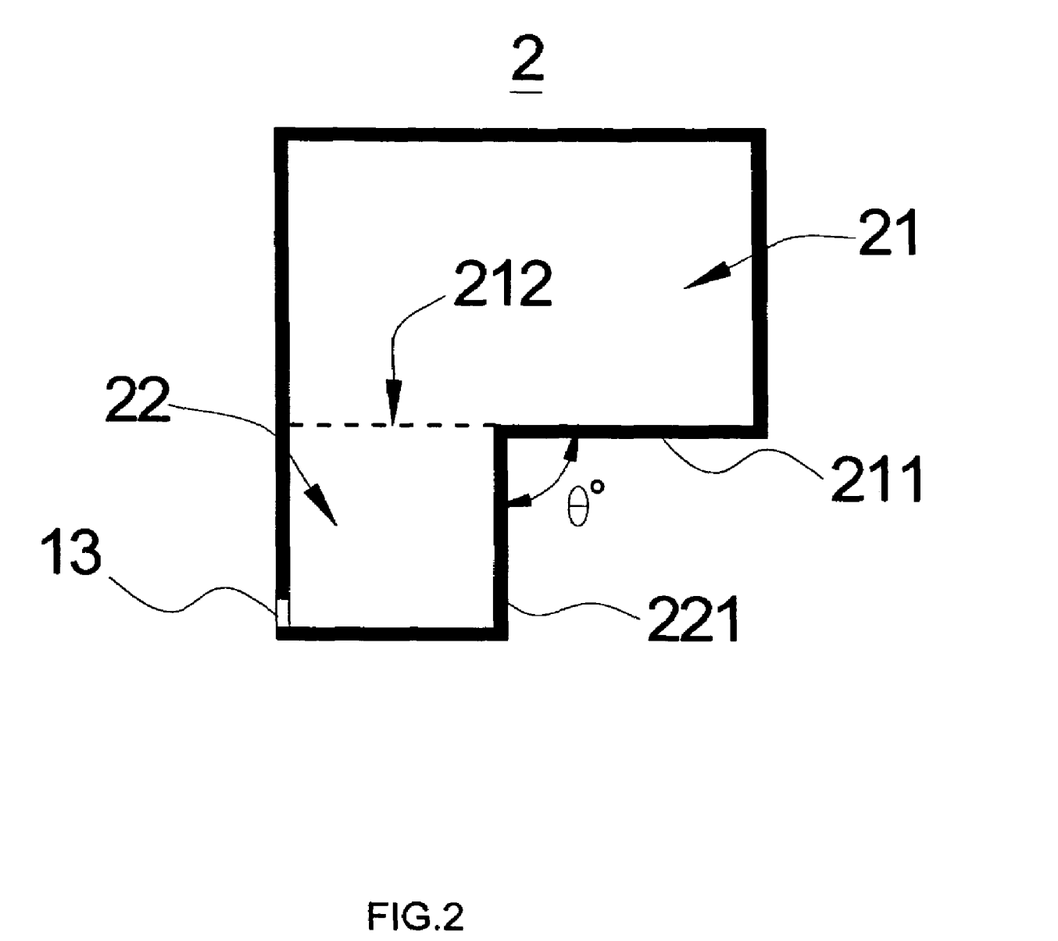
FIG. 2 is a schematic view of a cartridge structure according to a first embodiment of the present invention.

As shown in FIG. 2, the cartridge structure 2 comprises a first cartridge accommodation space 21 and a second accommodation space 22, wherein the first cartridge accommodation space 21 has a connection bottom 211 and a lower connection position 212. The second cartridge accommodation space 22 has a connection side 221 and an opening 13. The second cartridge accommodation space 22 is disposed under the lower connection position 212 of the first cartridge accommodation space 21, and the volume of the first cartridge accommodation space 21 is grater than the volume of the second cartridge accommodation space 22. The connection bottom 211 is vertically connected to the connection side 221 to form a right angle θ° that is equivalent to 90 degree.

Figure 3:
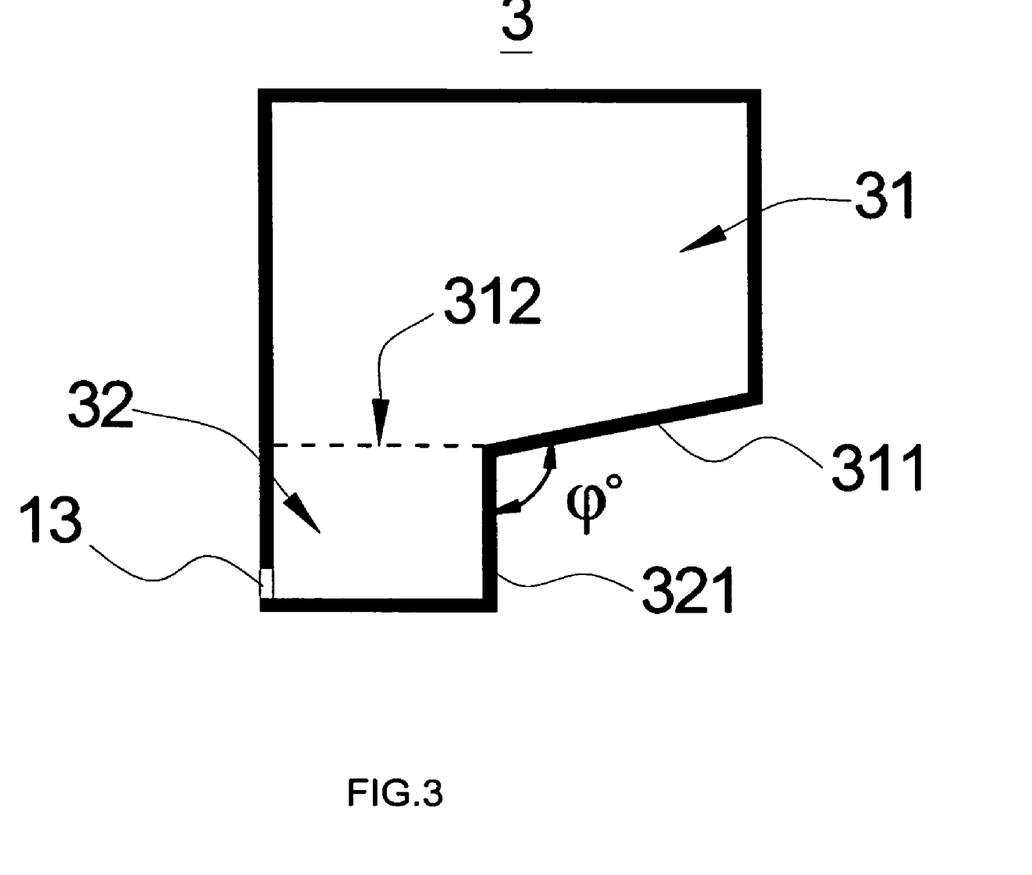
FIG. 3 is a schematic view of a cartridge structure according to a second embodiment of the present invention.

As shown in FIG. 3, the cartridge structure 3 comprises a first cartridge accommodation space 31 and a second cartridge accommodation space 32, wherein the first cartridge accommodation space 31 includes a connection bottom 311 and a lower connection position 312. The second cartridge accommodation space 32 has a connection side 321 and an opening 13. The second cartridge accommodation space 32 is disposed under the lower connection position 312 of the first cartridge accommodation space 31. The volume of the first cartridge accommodation space 31 is greater than the volume of the second cartridge accommodation space 32. The connection bottom 311 downwardly inclines toward the connection side 321 to form an included angle φ that is greater than 90 degree.

Figure 4:
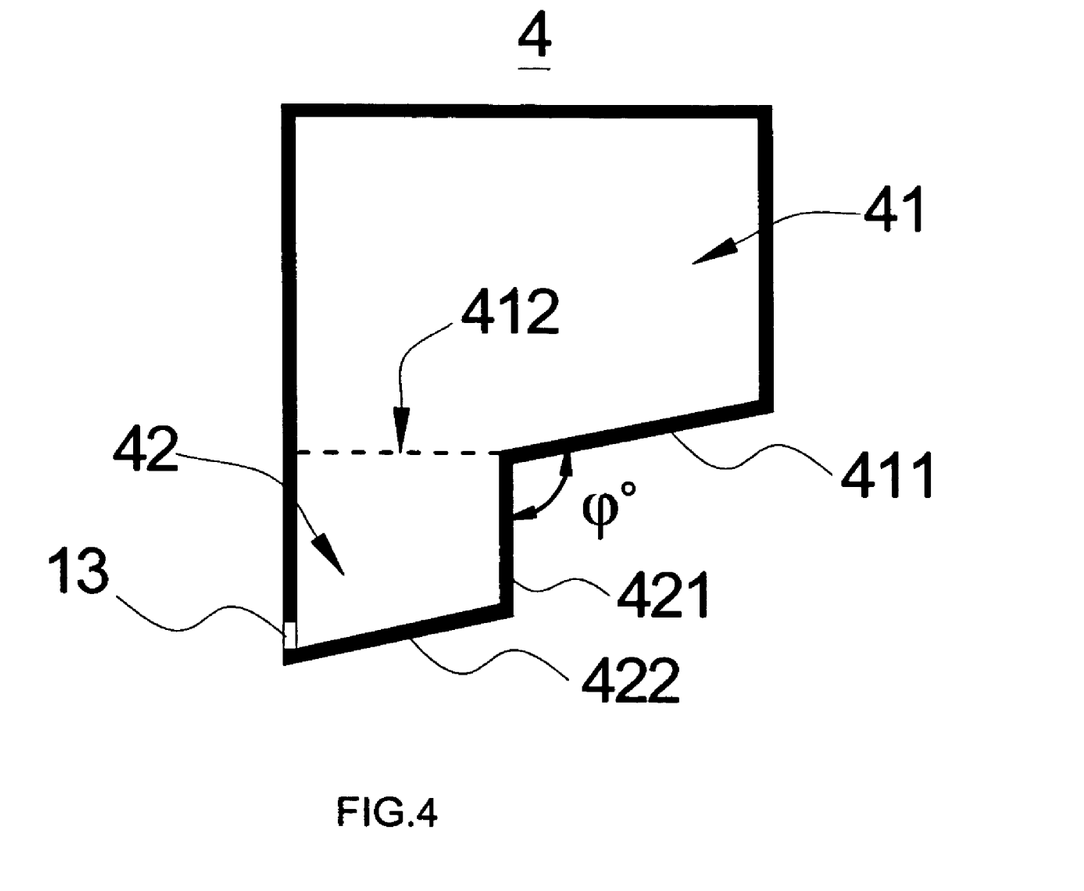
FIG. 4 is a schematic view of a cartridge structure according to a third embodiment of the present invention.

As shown in FIG. 4, the cartridge structure 4 comprises a first cartridge accommodation space 41 and a second cartridge accommodation space 42. The first cartridge accommodation space 41 includes a connection bottom 411 and a lower connection position 412, and the second cartridge accommodation space 42 includes a connection side 421, a bottom 422 and an opening 13. The second cartridge accommodation space 42 is disposed under the lower connection position 412 of the first cartridge accommodation space 41. The volume of the first cartridge accommodation space 41 is greater than the volume of the second cartridge accommodation space 42. The connection bottom 411 downwardly inclines toward the connection side 421 to form an included angle φ that is greater than 90 degree. Moreover, the bottom 422 downwardly inclines toward the opening 13 to allow liquid medicament to be supplied to the opening 13.

The connection sides 221, 321 or 421 also have inclination variation, and are combined with the connection bottoms 211, 311 or 411 as shown in FIG. 2 to FIG. 4 or variations of the bottoms of the second cartridge accommodation spaces 22, 32 or 42 to form inclination variations with different types.

Figure 5:
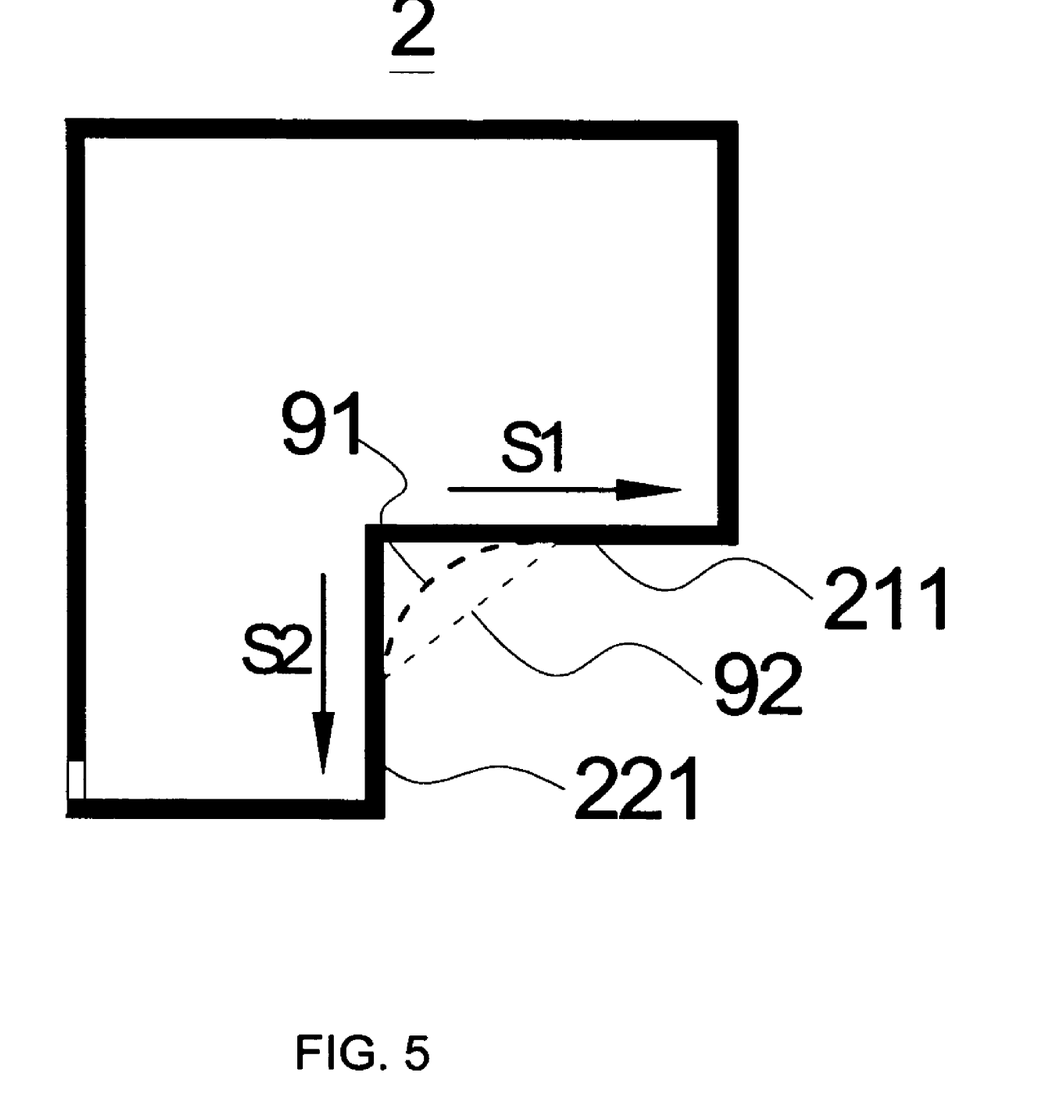
FIG. 5 is a schematic view of a cartridge structure according to the first embodiment of the present invention.

Furthermore, the right angle θ and the included angles φ as shown in FIG. 2 to FIG. 4 can be further changed to become lead angles. As shown in FIG. 5, the variation is upon the structure shown in FIG. 2, the right angle θ can be changed to become a fillet angle 91 or a chamfering angle 92. The fillet angle 91 is an arc formed between the connection bottom 211 and the connection side 221, and the chamfering angle 92 is an oblique angle formed between the connection bottom 211 and the connection side 221. The fillet angle 91 or the chamfering angle 92 can further extend toward directions indicated by arrows S1 and S2.

Figure 6:
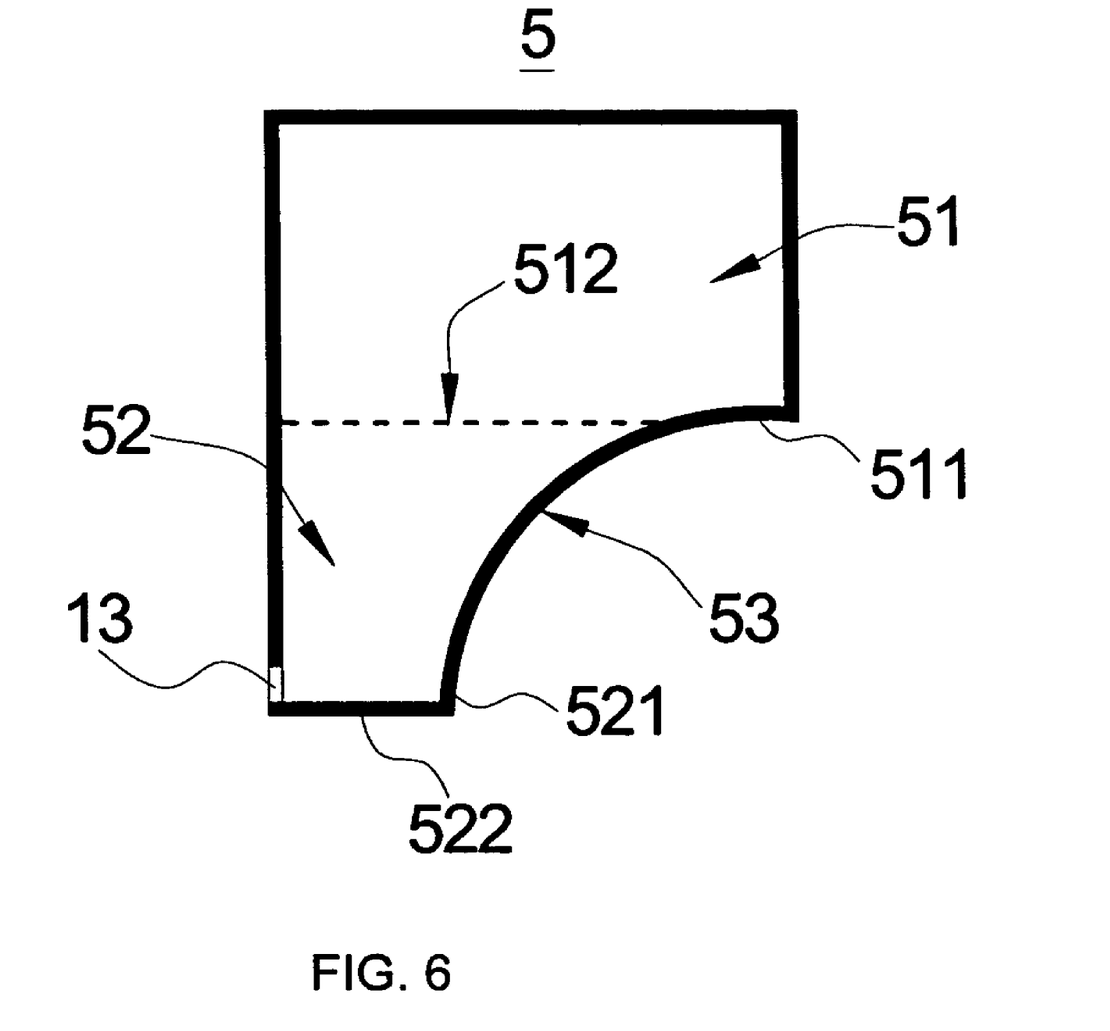
FIG. 6 is a schematic view of a cartridge structure according to a fourth embodiment of the present invention.

Therefore, as shown in FIG. 6, the cartridge structure 5 comprises a first cartridge accommodation space 51 and a second cartridge accommodation space 52. The first cartridge accommodation space 51 includes a connection bottom 511 and a lower connection position 512. The second cartridge accommodation space 52 includes a connection side 521, a bottom 522 and an opening 13. The second cartridge accommodation space 52 is disposed under the lower connection position 512 of the first cartridge accommodation space 51, and the volume of the first cartridge accommodation space 51 is greater than the volume of the second cartridge accommodation space 52. The connection bottom 51 is connected to the connection side 521 to form an included angle that is a fillet angle 53, and the connection side 521 and the connection bottom 511 are at two ends of the fillet angle 53 respectively so that the connection bottom 511 and the connection side 521 are connected together to become an arc. Moreover, the connection of the connection bottom 511 and the connection side 521 is toward the lower portion of the second cartridge accommodation space 52 to form a cambered surface. The fillet angle 53 includes a bottom 522 connected to an end of the connection side 521, and another end is at the side bottom end of the first cartridge accommodation space 51. Furthermore, the fillet angle 53 can also be replaced with a chamfering angle. The difference between the fillet angle and the chamfering angle is that the chamfering angle enables the connection bottom 511 and the connection side 521 to be intersected to compose an oblique angle, and the fillet angle 53 is an arc formed between the connection bottom 511 and the connection side 521, thereby increasing flexibility of space application.

Figure 7:
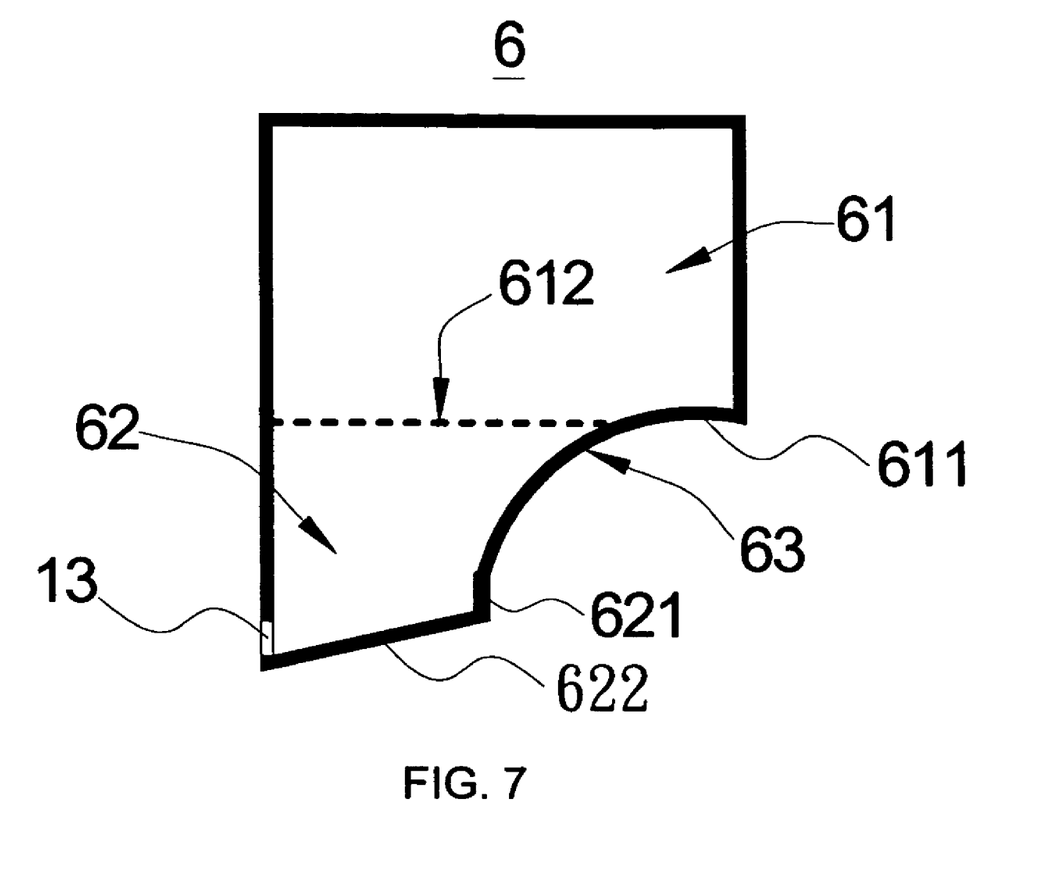
FIG. 7 is a schematic view of a cartridge structure according to a fifth embodiment of the present invention.

As shown in FIG. 7, another variation in accordance with the cartridge structure 5 as shown in FIG. 6, the cartridge structure 6 comprises a first cartridge accommodation space 61 and a second cartridge accommodation space 62. The first cartridge accommodation space 61 includes a connection bottom 611 and a lower connection position 612. The second cartridge accommodation space 62 has a connection side 621, a bottom 622 and an opening 13. The second cartridge accommodation space 62 is disposed under the lower connection position 612 of the first cartridge accommodation space 61, and the volume of the first cartridge accommodation space 61 is greater than the volume of the second cartridge accommodation space 62. The connection bottom 611 is connected to the connection side 621 to form an included angle that is a fillet angle 63. The connection side 621 and the connection bottom 611 are at two sides of the fillet angle 63 respectively so that the connection bottom 611 and the connection side 621 are connected together to become an arc. The connection of the connection bottom 611 and the connection side 621 is toward the lower portion of the second cartridge accommodation space 62 to form a cambered surface. The fillet angle 63 includes a bottom 622 connected to an end of the connection side 621, and another end is at the side bottom end of the first cartridge accommodation space 61. Moreover, the difference between the embodiment and FIG. 6 is that the bottom 622 downwardly inclines toward the opening 13 to allow liquid medicament to be supplied to the opening 13. Furthermore, the fillet angle 63 can be replaced with the chamfering angle. The difference between the fillet angle and the chamfering angle is that the chamfering angle enables the connection bottom 611 and the connection side 621 to be intersected to compose an oblique angle, and the fillet angle 63 is an arc formed between the connection bottom 611 and the connection side 621, thereby increasing flexibility of space application.

Figure 8:
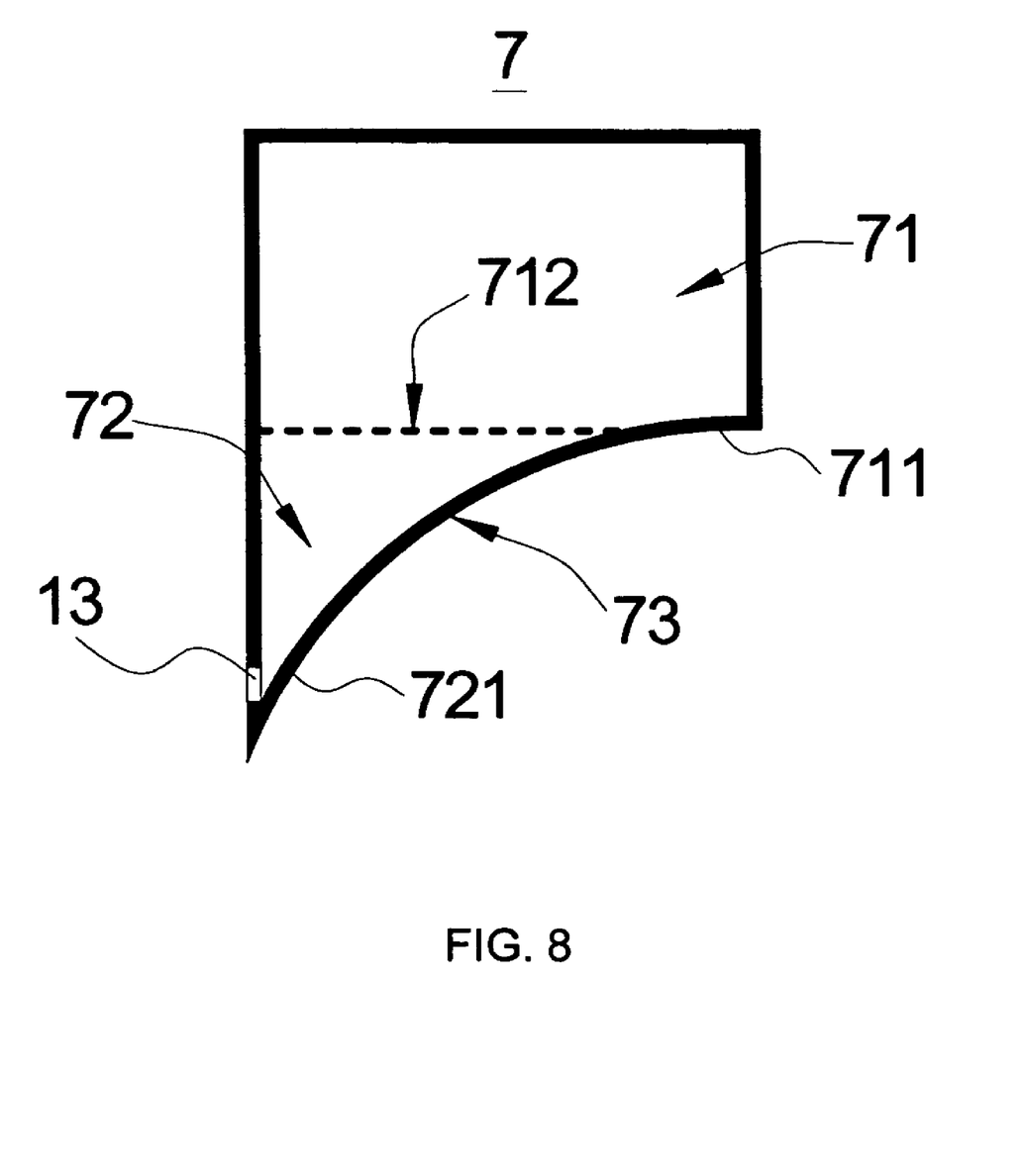
FIG. 8 is a schematic view of a cartridge structure according to a sixth embodiment of the present invention.

As shown in FIG. 8, a further variation in accordance with the cartridge structure 5 and 6 as shown in FIG. 6 and FIG. 7, the cartridge structure 7 comprises a first cartridge accommodation space 71 and a second cartridge accommodation space 72. The first cartridge accommodation space 71 includes a connection bottom 711 and a lower connection position 712. The second cartridge accommodation space 72 includes a connection side 721 and an opening 13. The second cartridge accommodation space 72 is disposed under the first cartridge accommodation space 71, and the volume of the first cartridge accommodation space 71 is greater than the volume of second the cartridge accommodation space 72. The connection bottom 711 is connected to the connection side 721 to form an included angle that is a fillet angle 73. The connection side 721 and the connection bottom 711 are at two sides of the fillet angle 73 respectively so that the connection bottom 711 and the connection side 721 are connected together to become an arc. Moreover, the connection of the connection bottom 711 and the connection side 721 is toward the lower portion of the second cartridge accommodation space 72 to form a cambered surface. The difference between the embodiment and the FIG. 6 and FIG. 7 is that the radius of the fillet angle 73 is the maximum value that expands the fillet angle to be the maximum so that the second cartridge accommodation space 72 does not have the bottom 622 as shown in FIG. 6. Accordingly, the fillet angle 73 includes the connection side 721 directly connected to the side wall of the opening 13 of the second cartridge accommodation space 72, and another end is at the side bottom end of the first cartridge accommodation space 71. Furthermore, the fillet angle 73 can be replaced with the chamfering angle. The difference between the fillet angle and the chamfering angle is that the chamfering angle enables the connection bottom 711 and the connection side 721 to be intersected to compose an oblique angle, and the fillet angle 73 is an arc formed between the connection bottom 711 and the connection side 721, thereby increasing flexibility of space application.

Figure 9:
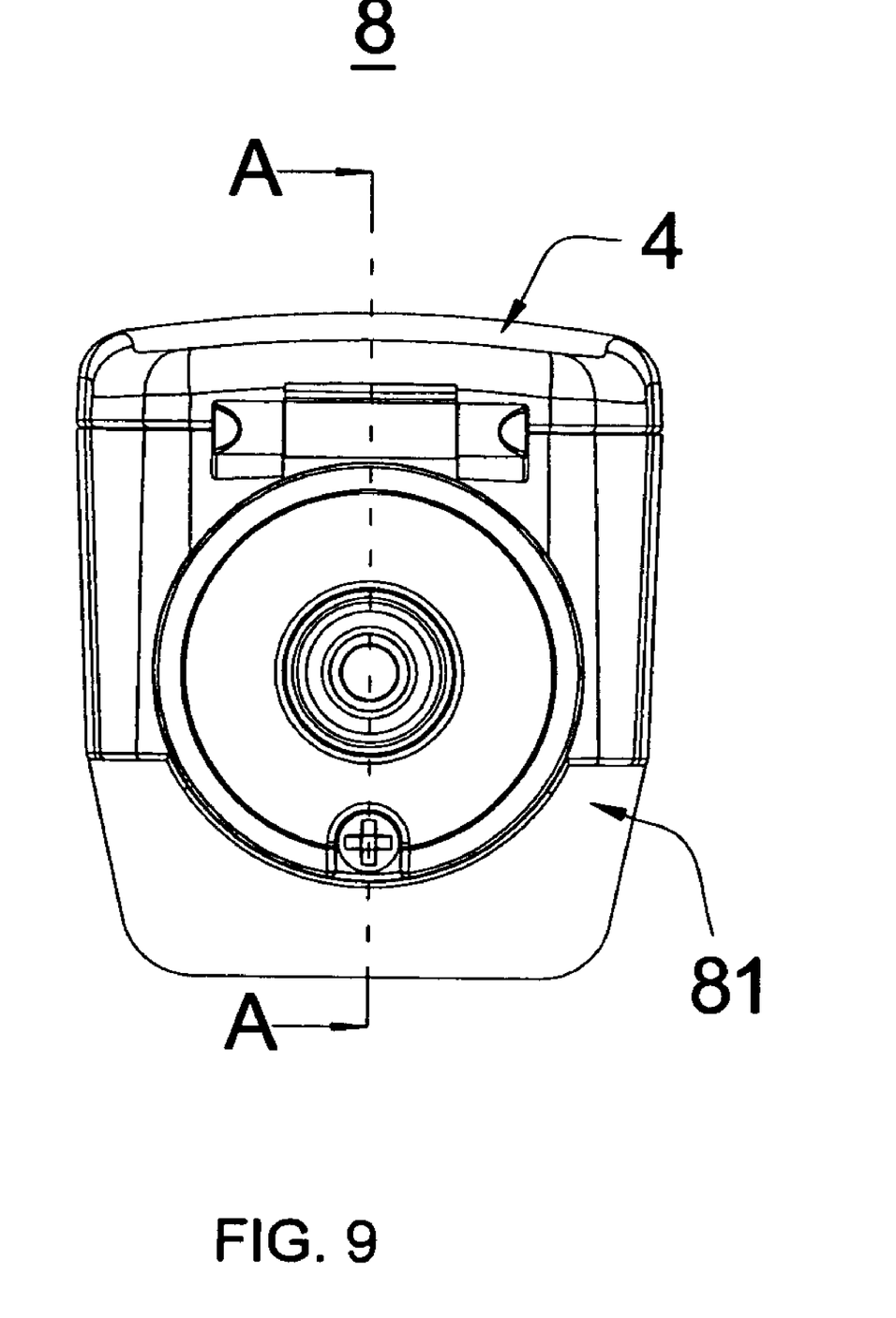
FIG. 9 is a front view of a nebulizer according to a preferred embodiment of the present invention.
Figure 10:
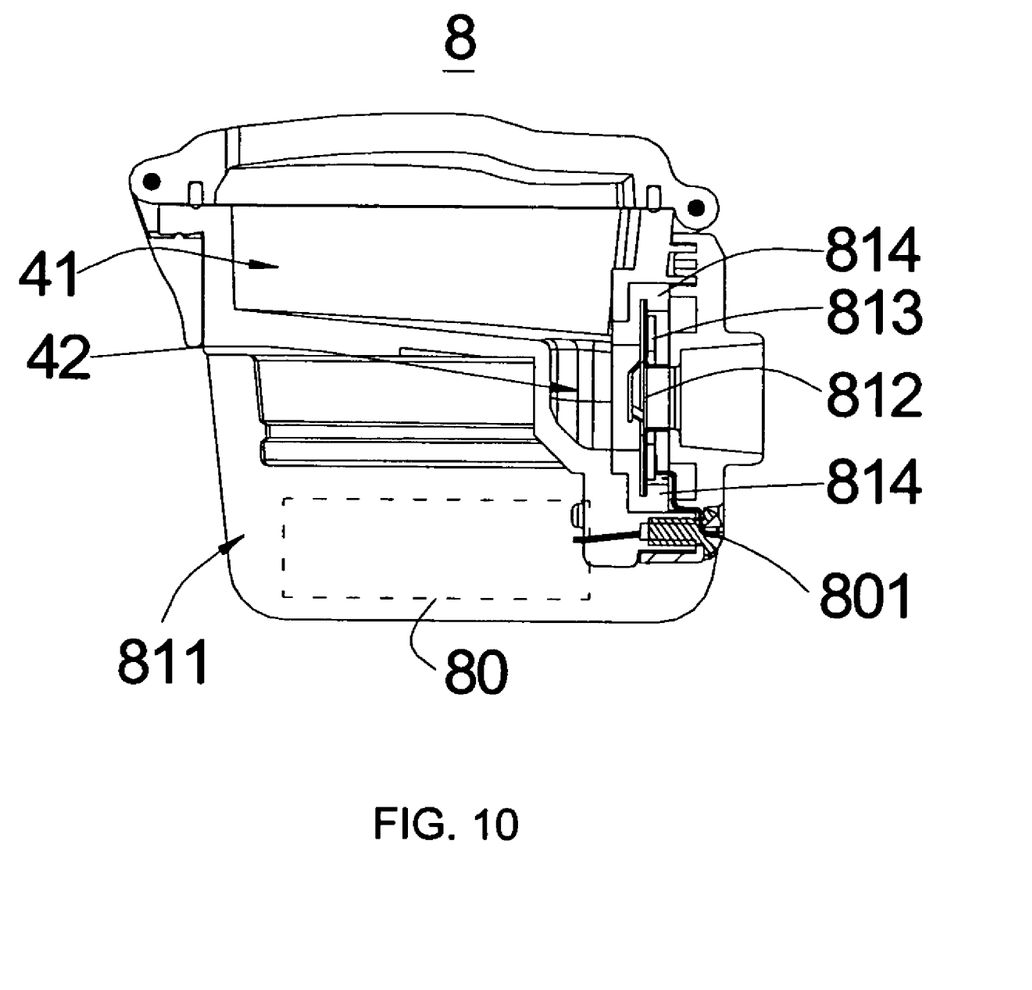
FIG. 10 is a cross-sectional drawing of a nebulizer according to a preferred embodiment of the present invention.

Referring to FIG. 9 for the front view shows a nebulizer according to a preferred embodiment of the invention. The nebulizer 8 comprises a nebulizing device 81 and the cartridge structure 4. Moreover, referring to FIG. 10 for the cross-sectional drawing shows the nebulizer according to a preferred embodiment of the invention. The line segment AA shown in FIG. 9 is taken to be the section for FIG. 10, and then the internal structures of the nebulizing device 81 and the cartridge structure 4 can be clearly seen. The cartridge structure 4 comprises the first cartridge accommodation space 41 and the second cartridge accommodation space 42. The nebulizing device 81 comprises a nebulizer main body 811, a nozzle disc 812, a vibratable member 813 and a housing 814. The nebulizer main body 811 has a controlling element 80, and the nozzle disc 812 is disposed to the opening 13 of the second cartridge accommodation space 42. The vibratable member 813 is combined with the nozzle disc 812, and connected to a contact 801 of the controlling element 80, thereby electrically connecting the controlling element 80. The housing 814 is used to cover up the nozzle disc 812 and the vibratable member 813. The vibratable member 813 is preferably a piezoelectric member. The housing 814 provides fastening mechanism. Accordingly, the nebulizer 8 can utilize electronic aerosol technology (e.g., piezoelectric nozzle method) to be the operating mechanism for aerosolizing liquid medicaments.

Moreover, at least one plane of the periphery of the openings 13 of the cartridge structure 2, 3, 4, 5, 6 or 7 and the second cartridge accommodation space 22, 32, 42, 52, 62 or 72 form a co-plane. The connection bottoms 211, 311, 411, 511, 611 and 711 and the connection sides 221, 321, 421, 521, 621 and 721 are preferably cambered surfaces, curved surfaces or planes, and the bottoms 422, 522 and 622 are preferably cambered surfaces, curved surfaces or planes, and the maximum scope expanded from the chamfering angle forms an inclination, and the maximum scope expanded from the radius of the fillet angle forms an arc. Meanwhile, the residues of liquid medicament can be efficiently eliminated through any combination of various shapes.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A cartridge structure for a nebulization apparatus, the cartridge structure comprising:
   a first cartridge accommodation space; and
   a second cartridge accommodation space disposed under a lower connection position of the first cartridge accommodation space, and at least one connection side of the second cartridge accommodation space being connected to a connection bottom of the first cartridge accommodation space to form an included angle, wherein said second cartridge accommodation space has an opening, and said nebulization apparatus further comprises:
   a nebulizer main body having at least one controlling element;
   a nozzle disc disposed adjacent to said opening in the second cartridge accommodation space; and
   a vibratable member connected to said nozzle disc, said vibratable member being electrically connected to said at least one controlling element.

2. The cartridge structure of claim 1, wherein the nebulization apparatus further includes a housing for covering the nozzle disc and the vibratable member.

3. The cartridge structure of claim 1, wherein the vibratable member is a piezoelectric member.

4. A nebulizer comprising:
   a nebulization apparatus; and
   a cartridge structure having a first cartridge accommodation space and a second cartridge accommodation space,
   wherein the second cartridge accommodation space is disposed under a lower connection position of the first cartridge accommodation space, and
   at least one connection side of the second cartridge accommodation space is connected to a connection bottom of the first cartridge accommodation space to form an included angle, wherein said second cartridge accommodation space has an opening, and said nebulization apparatus further comprises:
   a nebulizer main body having at least one controlling element;
   a nozzle disc disposed adjacent to said opening in said second cartridge accommodation space; and
   a vibratable member connected to said nozzle disc, said vibratable member being electrically connected to said at least one controlling element.

5. The nebulizer of claim 4, wherein the nebulization apparatus further comprises a housing for covering the nozzle disc and the vibratable member.

6. The nebulizer of claim 4, wherein the vibratable member is a piezoelectric member.

* * * * *